United States Patent [19]
Lee

[11] Patent Number: 6,140,136
[45] Date of Patent: Oct. 31, 2000

[54] ANALYTICAL TEST DEVICE AND METHOD OF USE

[75] Inventor: Jin Po Lee, Poway, Calif.

[73] Assignee: Syntron BioResearch, Inc., Carlsbad, Calif.

[21] Appl. No.: 09/156,770

[22] Filed: Sep. 18, 1998

[51] Int. Cl.⁷ ............................................. G01N 33/533
[52] U.S. Cl. .................. 436/518; 436/524; 436/530; 436/541; 436/807; 435/7.1; 435/7.93; 435/7.94; 435/287.7; 435/287.9; 435/288.7; 435/970; 422/56; 422/99; 422/58; 422/104; 422/59; 422/60
[58] Field of Search ................................. 436/518, 524, 436/530, 541, 807; 435/7.1, 7.93, 7.94, 287.7, 287.9, 288.7, 970; 422/56, 99, 58, 104, 59, 60

[56] References Cited

U.S. PATENT DOCUMENTS

| 3,868,219 | 2/1975 | Hurenkamp | 23/230 |
|---|---|---|---|
| 3,884,641 | 5/1975 | Kraffczyk et al. | 23/253 |
| 4,046,514 | 9/1977 | Johnston et al. | 23/253 |
| 4,059,407 | 11/1977 | Hochstrasser | 23/253 |
| 4,168,146 | 9/1979 | Grubb et al. | 23/230 |
| 4,200,690 | 4/1980 | Root et al. | 435/7 |
| 4,703,017 | 10/1987 | Campbell et al. | . |
| 4,874,691 | 10/1989 | Chandler et al. | . |
| 4,916,056 | 4/1990 | Brown, III et al. | . |
| 4,943,522 | 7/1990 | Eisinger et al. | 435/7 |
| 4,956,302 | 9/1990 | Gordon et al. | 436/161 |
| 5,008,080 | 4/1991 | Brown, III et al. | 422/56 |
| 5,145,789 | 9/1992 | Corti et al. | 436/530 |
| 5,149,622 | 9/1992 | Brown et al. | 435/5 |
| 5,160,701 | 11/1992 | Brown, III et al. | 422/56 |
| 5,275,785 | 1/1994 | May et al. | 422/56 |
| 5,384,264 | 1/1995 | Chen et al. | 436/525 |
| 5,416,000 | 5/1995 | Allen et al. | . |
| 5,504,013 | 4/1996 | Senior | . |
| 5,558,834 | 9/1996 | Chu et al. | 422/55 |
| 5,559,041 | 9/1996 | Kang et al. | 436/518 |
| 5,591,645 | 1/1997 | Rosenstein | 436/514 |
| 5,602,040 | 2/1997 | May et al. | 436/514 |
| 5,622,871 | 4/1997 | May et al. | 436/514 |
| 5,648,269 | 7/1997 | Lakowicz et al. | 436/68 |
| 5,656,503 | 8/1997 | May et al. | 436/514 |
| 5,660,991 | 8/1997 | Lakowicz et al. | 435/7.1 |
| 5,714,389 | 2/1998 | Charlton et al. | 436/514 |
| 5,726,010 | 3/1998 | Clark | 435/5 |
| 5,728,587 | 3/1998 | Kang et al. | 436/518 |
| 5,739,041 | 4/1998 | Nazareth et al. | 436/518 |
| 5,820,826 | 10/1998 | Moorman | 422/104 |
| 5,900,379 | 5/1999 | Noda et al. | . |

FOREIGN PATENT DOCUMENTS

| 0 250 137 B1 | 12/1987 | European Pat. Off. | G01N 33/558 |
|---|---|---|---|
| 0 291 194 B1 | 11/1988 | European Pat. Off. | G01N 33/543 |
| 0 560 410 A2 | 9/1993 | European Pat. Off. | G01N 33/52 |
| 2 204 398 | 11/1988 | United Kingdom . | |
| 88/08534 | 11/1988 | WIPO | G01N 33/543 |

*Primary Examiner*—James C. Housel
*Assistant Examiner*—Bao-Thuy L. Nguyen
*Attorney, Agent, or Firm*—Campbell & Flores LLP

[57] ABSTRACT

The present invention provides an analytical test device for conducting assays of biological fluids. Methods for carrying out the assays with the disclosed analytical test device are also provided.

13 Claims, 6 Drawing Sheets

ANALYTICAL TEST DEVICE AND METHOD OF USE

FIELD OF THE INVENTION

This invention relates to a novel analytical test device for analysis of biological fluids such as urine. The invention further relates to methods for detecting analytes in fluids using the test device.

BACKGROUND INFORMATION

The sampling and testing of biological fluids such as urine for the presence of analytes provide important information regarding various health-related matters, including pregnancy and conception.

In recent years, test devices have undergone nearly continuous refinement in an effort to simplify and speed the process of detecting selected ligand in fluids. As a result of this work, current test devices use an immunoassay for determining pregnancy or conception. In these devices a reagent, such as an antibody, specifically reacts with an analyte to form a complex, which can usually be detected by the unaided eye.

Current pregnancy test devices assay for hormones associated with pregnancy, such as, for example, chorionic gonadotrophin (hereinafter "hCG") since the presence of hCG in urine is usually an indicator that a woman is pregnant. Such test devices obtain qualitative results indicating either the presence or absence of hCG. Typically, a pregnancy immunoassay contains an antibody directed against hCG. The reaction complex can then be viewed by the user.

Conception test devices also assay for hormones associated with the ovarian cycle, such as, for example, luteinizing hormone (hereinafter "LH"). LH is present normally in urine but its concentration increases markedly during ovulation, the time at which a woman is most likely to conceive. Thus, the probability that a woman can conceive a child varies directly with LH concentration. Such test devices obtain semi-quantitative results regarding the relative concentration of LH in the urine. Typically, a conception immunoassay contains an antibody directed against LH and a separate detection antibody.

In known devices, the fluid to be tested wicks up through an absorbent membrane that is in fluid flow contact with the reagents that detect an analyte in a fluid. A major problem with this type of device is that as the fluid progresses through the membrane, the front edge of the fluid is uneven. The uneven fluid front will cause the results to be smeared, produce false negatives and make the results difficult to detect. These artifacts are called "leading edge effects." An uneven fluid front can arise for a variety of reasons, for example, because the sample is not uniformly applied to the absorbent membrane.

Therefore, a need exists for a device that does not produce an uneven fluid front and associated leading edge effects. The present invention provides a device that eliminates the uneven fluid front problem and related methods of using such a device.

SUMMARY OF THE INVENTION

The present invention provides an analytical test device for analyzing biological fluids, for example, urine. The device has a top with one or more display ports and, optionally, a receiving port and a vertical bar. The device also has a bottom and, optionally, a receiving port, an upper plane, a slope and a lower plane. The device further has a strip made up of an absorbent membrane, a reaction membrane with one or more reagents that form a reaction complex with an analyte in a fluid sample and, optionally, a collecting pad. The device also has an absorbent sample pad in a container and a stopping means.

The absorbent membrane, the reaction membrane and the collecting pad, when present, are in fluid flow contact with one another. The strip is placed on the bottom such that the reaction membrane is visible through the display port and the absorbent membrane is toward the receiving port. The top or the bottom has the receiving port or together the top and the bottom form the receiving port and in the assembled top and bottom the absorbent sample pad is slidably insertable through the receiving port until stopped by the stopping means, which places the absorbent sample pad in fluid flow contact with the absorbent membrane.

In one embodiment, the analytical test device also has the top with the optional vertical bar. The vertical bar deflects the absorbent membrane to follow the contour of the slope. The bottom has the optional lower plane, upper plane and slope and also a stopping means.

The present invention also provides methods for detecting an analyte in a fluid sample, comprising adding fluid sample to the absorbent sample pad, inserting the absorbent sample pad into the receiving port until the absorbent sample pad is stopped by the stopping means and detecting the analyte by observing the reaction complex through the display port. In one method the reaction complex is visible.

DETAILED DESCRIPTION OF THE INVENTION

The present invention is directed to an analytical test device that eliminates the uneven fluid front and leading edge effects associated with prior devices. The analytical test device ensures that fluid sample comes into fluid flow contact with the membrane that contains the reagents to detect the analyte, evenly and at the same height across the membrane, thereby producing an even fluid front.

Fluid sample is collected in an absorbent sample pad that is initially not in fluid flow contact with the absorbent membrane. Then the absorbent sample pad is contacted to the absorbent membrane so that the fluid sample comes into fluid flow contact with the absorbent membrane. The edge of the absorbent sample pad contacts the absorbent membrane orthogonal to the absorbent membrane, ensuring that the fluid sample will contact the absorbent membrane evenly and at the same height across the membrane.

A further advantage of the analytical test device is that the user can control when the assay starts. Thus, if desired, the user can add more than one fluid sample to the absorbent sample pad before the assay starts. This feature is especially important where the user only wishes to know whether an analyte is present in more than one fluid sample. In prior devices, once the fluid sample is added, the assay proceeds and the reagents are depleted before a second sample can be added. Thus, the user is not given the time to test additional samples.

The analytical test device of the present invention includes a top and a bottom. The top has a display port that allows the user to see the results. Preferably, the top will have a first display port and a second display port that are in close proximity for easy comparison of results. The bottom has a receiving port for an absorbent sample pad. Inside the device is a strip formed by an absorbent membrane, a reaction membrane and, optionally, a collecting pad. The absorbent membrane and the reaction membrane contain the reagents to detect an analyte in the fluid sample. When the top is placed on the bottom in the assembled device, the absorbent membrane will be positioned on the bottom toward the receiving port and the reaction membrane will be positioned on the bottom underneath the display port.

The absorbent sample pad is held in a container. In one embodiment, the absorbent sample pad will be protruding from the container. Fluid sample is deposited on the absorbent sample pad and, if desired, more than one fluid sample can be applied or contacted with the absorbent sample pad before the test is allowed to proceed. At this point the absorbent sample pad is not in fluid flow contact with the strip. The absorbent sample pad is then inserted into the receiving port until the absorbent sample pad is in fluid flow contact with the absorbent membrane. The analytical test device also has a stopping means that prevents the absorbent sample pad from reaching far enough into the assembled top and bottom to by-pass the absorbent membrane and contact the reaction membrane.

The bottom of the analytical test device of the present invention can also be divided into an upper plane and a lower plane by a slope. As used herein, the term "slope" refers to a surface or plane of the bottom of the device that is at such an angle in relation to the other planes of the bottom that it slows the rate of fluid sample wicking through the absorbent membrane. Thus, the slope prevents an excess amount of fluid sample migrating through the absorbent membrane, which would otherwise and compromise the assay.

When the slope is present, the absorbent membrane is along the lower plane and the slope and the reaction membrane is on the upper plane. Also, the analytical test device has a vertical bar extending downward from the top. As used herein, the term "vertical bar" refers to a part of the top of the device extending downward from the top at a point just in front of the slope that holds or deflects the absorbent membrane to follow the contour of the slope. Optionally, the vertical bar can extend downward far enough to only allow fluid sample to proceed further into the device by wicking through the absorbent membrane.

In one embodiment, the absorbent sample pad is inside a container that can be slidably inserted through the receiving port until it comes into fluid flow contact with the absorbent membrane. In a further embodiment, the absorbent sample pad is in a container separate from the assembled top and bottom. The absorbent sample pad protrudes from the container and can be inserted into the receiving port. In another embodiment, the absorbent sample pad is in a container that is disposed between the assembled top and bottom of the analytical test device, and partially protruding therefrom. A knob attached to the container allows the user to slide the container inside the device until the stopping means stops the container and the absorbent sample pad contacts the absorbent membrane.

An amount of fluid sample, such as urine, which is suspected of containing, for example hCG, is applied by dropping or pouring (from a pipette or other container) the sample onto the absorbent sample pad. Alternatively, in one embodiment, the absorbent sample pad can be dipped into a fluid sample. In addition, the absorbent sample pad may be wetted by carefully holding in a stream of urine. The absorbent sample pad is then contacted with the absorbent membrane by inserting the absorbent sample pad through the receiving port until the container is stopped by the stopping means.

The fluid sample then proceeds by capillary action (i.e., wicking) through the absorbent membrane. Bound evenly and at the same height extending from side to side of the absorbent membrane, at a downstream point spatially separated from the point where the absorbent sample pad contacts the absorbent membrane and downstream from the vertical bar is a diffusively bound labeled reagent. The spatial separation ensures that the fluid sample wicks up through the absorbent membrane to contact the diffusively bound labeled reagent. Thus, the diffusively bound labeled reagent stays within the absorbent membrane and does not migrate into the fluid sample, which would otherwise destroy the performance of the assay.

If analyte is present in the fluid sample it will complex with the diffusively bound labeled reagent. Fluid sample containing either diffusively bound labeled reagent alone or a diffusively bound labeled reagent/analyte complex (i.e., "first complex") will move by wicking up to a "test region" in the reaction membrane. Bound evenly and at the same height extending from side to side of the reaction membrane in the test region is a non-diffusively bound reagent capable of complexing the first complex. The non-diffusively bound reagent may be non-diffusively bound to the membrane by means known in the art, including covalent bonding or attachment to an insoluble protein-coated surface (see, for example, U.S. Pat. No. 4,200,690, which is incorporated herein by reference). Preferably, the non-diffusively bound reagent will be bound in a bar shape extending from side to side of the reaction membrane in a manner similar to the attachment of the diffusively bound labeled reagent to the absorbent membrane.

If a first complex is present in the fluid sample, the analyte portion of the first complex will bind to the non-diffusively bound reagent creating a detectable signal, preferably a visible straight line or bar extending from side to side of the reaction membrane at the first display port. As a control, fluid sample will continue its migration past the first display port to a "control region" portion of the reaction membrane.

The control region is so called because bound evenly and at the same height extending from side to side of the reaction membrane is a non-diffusively bound control reagent. The diffusively bound labeled reagent, complexed with analyte or not, will bind to the non-diffusively bound control reagent present in the control region. This binding will create a detectable signal, preferably a visible straight line or bar extending from side to side of the reaction membrane at the second display port. For ease of comparison, the shape and orientation of the non-diffusively bound control reagent should be similar to the shape and orientation of the non-diffusively bound reagent. In addition, the non-diffusively bound control reagent may be non-diffusively bound in the manner similar to that of the non-diffusively bound reagent, described above. When the top is aligned with the bottom in the assembled device the diffusively bound labeled reagent will be bound so as to be spatially separated from the point where the absorbent sample pad contacts the absorbent membrane, the non-diffusively bound reagent will be bound beneath first display port and the non-diffusively bound control reagent will be bound beneath second display port.

The results can then be interpreted. If a signal appears at the first display port and a signal appears at the second display port, the test is positive for the presence of analyte. If there is no signal detectable at the first display port compared to the signal at the second display port, the test is negative for the presence of analyte. If there is no signal at the second display port, the user is alerted that the test results are compromised and that the test should be repeated.

Alternatively, the analytical test device can employ a competitive assay system. A diffusively bound labeled reagent capable of competing with the analyte for a non-diffusively bound reagent is applied evenly and at the same height extending from side to side of the absorbent membrane. It is applied at a downstream point spatially separated from the point where the absorbent sample pad contacts the absorbent membrane and downstream from the vertical bar. The diffusively bound labeled reagent here does not complex with the analyte. A non-diffusively bound reagent that can bind either the analyte or the diffusively bound reagent is applied evenly and at the same height extending from side to side of the reaction membrane at a point beneath the display port. In this embodiment of the analytical test device, the top need only have one display port, as no comparison is required. However, if desired, a second display port may be incorporated to demonstrate the integrity of the reagents and device. In this embodiment, the presence of a visible signal, such as a straight line or bar across the reaction membrane in the display port is a validation of the assay and indicates that no analyte is present in the fluid sample. No signal in the display port indicates the presence of analyte in the fluid sample.

The analytical test device allows the assay to be performed in simple steps. The user only has to apply the fluid sample, slide the absorbent sample pad into the receiving port to contact the absorbent sample pad with the absorbent membrane and then observe the results.

The analytical test device is assembled by placing the absorbent membrane and the reaction membrane on the bottom and then the top is then placed on the bottom to ensure a tight fit. One skilled in the art would understand that any suitable means to ensure a tight fit between the top and bottom can be used. For example, the top can be fitted on the bottom with snaps or glue. In addition, once the absorbent sample pad is inserted into the receiving port, the device becomes substantially fluid-tight and evaporation or leakage of the fluid sample is minimized. To further prevent such leakage, the top and bottom are preferably made of a nonporous plastic, such as the commercially available plastic "ABS" supplied by the Monsanto Company of St. Louis, Mo.

Several features of the analytical test device assist in avoiding compromised results. First, simultaneous migration of an excessive amount of fluid sample is limited by requiring the fluid sample to ascend the slope from the absorbent membrane to the reaction membrane. Second, the spatial separation of the diffusively bound labeled reagent on the absorbent membrane from the point at which the fluid sample first contacts the absorbent membrane ensures that the assay is not compromised by reagent leaking out into the fluid sample. Third, the impact of leading edge effects caused by depletion of bound reagents or labels are minimized by physically separating the test and control regions, by applying the fluid sample evenly and at the same height across the absorbent membrane and by using the presence of a reaction, rather than the appearance of a given shape (such as a "+" or a "−") to signify a positive or negative result. In addition, the entire process is simplified by having the label bound to a substrate placed within the analytical test device, thus avoiding any need for the user to add a reagent or mix it with fluid sample.

As described above, the present invention is also ideally suited to the application of more than one fluid sample to a single analytical test device. In prior devices, such as the one described in May et al., U.S. Pat. No. 5,602,040, issued Feb. 11, 1997, the device (hereinafter the '040 device) is typically held in a stream of urine. The protruding sample aperture in the '040 device is in contact with the dry porous carrier inside the hollow casing of the device. Thus, the test proceeds immediately upon application of the sample. Therefore, the '040 device is suited for the testing of only one sample at a time because once the first sample is applied, the test proceeds, thereby depleting the reagents.

Moreover, since the user of the '040 device typically holds the protruding bibulous member in a urine stream, the sample is unevenly applied to the membrane. Thus, the '040 device suffers from leading edge effects created by an uneven solvent front along the membrane. Accordingly, reagents and bound labels could be depleted and the results could be misleading. In contrast, the user of the present analytical test device is assured that the solvent front formed by the fluid sample will be uniform since the fluid sample is applied evenly and at the same height across the absorbent membrane. Therefore, the present analytical test device provides more reliable results.

As used herein, the terms "ligand" and "control reagent" are used interchangeably and refer to a molecule to which another molecule will bind. A ligand or control reagent can be human, animal or plant in origin. For purposes of this invention, these may include LH, hCG or other naturally occurring biological control reagents in serum, plasma, urine or other fluids and will preferably include analytes. Specifically, it will be appreciated by those skilled in the art that the control reagent or analyte may be a protein, peptide, amino acid, nucleic acid, sugar, hormone, steroid, vitamin, toxin in the sample fluid, pathogenic microorganism and metabolites from analogs of such analytes, or antibodies to these substances. They may also include hormones, haptens, immunoglobulin, polynucleotides, drugs and infectious disease agents (bacterial or viral) such as Streptoccus, Neisseria, Chlamydia, Gonorrhea and HIV.

As used herein, the term "reagent" refers to receptor molecules which bind to a control reagent. Reagents may, in this context, include any naturally occurring or synthetic biological receptor and will preferably include antibodies. The antibodies may be polyclonal or monoclonal. For simplicity, the terms antibody and analyte will be used interchangeably with reagent and control reagent, respectively, throughout this disclosure. It will be appreciated by those skilled in the art, however, that the invention is not limited to use with analytes and antibodies.

Ligand-reagent pairs useful in the present invention include specific binding pairs such as antigens and antibodies, or fragments of antibodies, both polyclonal and monoclonal, lectins and carbohydrates, hormones and hormone receptors, enzymes and enzyme substrates, biotin and avidin, vitamins and vitamin binding proteins, complementary polynucleotide sequences, drugs and receptors, enzymes and inhibitors, apoproteins and cofactors, growth factors and receptors, and the like. Biotin and avidin derivatives may also be used, including biotin analogs/avidin, biotin/streptavidin, and biotin analogs/streptavidin. Members of the complex may be "engineered," that is, made by synthetic means. Such techniques are well known in the art, and include techniques for chimeric and humanized antibodies and fragments thereof, synthetic peptides, and synthetic RNA and DNA oligonucleotides.

Any known reagent can be used in any known format such as, for example, sandwich and competitive binding formats, to specifically detect an analyte in a fluid sample. Examples of such reagents are those disclosed in: H. J. Friesen, U.S. Pat. No. 4,861,711, issued Aug. 29, 1989; J. Bunting, U.S. Pat. No. 4,271,140, issued Jun. 2, 1981; May et al., U.S. Pat. No. 5,622,871, issued Apr. 22, 1997; May et al., U.S. Pat. No. 5,656,503, issued Aug. 12, 1997; May et al., U.S. Pat. No. 5,602,040, issued Feb. 11, 1997; and R. Rosenstein, U.S. Pat. No. 5,591,645, issued Jan. 7, 1997 (each of which is incorporated by reference herein). Such reagents can form a detectable complex with such control reagents as listed above.

Preferred reagents include antibodies to a hormone or infectious disease agent. Preferred antibodies include anti-hCG antibodies and anti-human LH antibodies, especially of the IgG class, and even more so murine monoclonal antibodies and especially those that have been affinity purified. One skilled in the art would recognize, however, that polyclonal antibodies can also be used in the present invention.

By the term "non-diffusively bound" is meant covalent or non-covalent attachment to the absorbent membrane or reaction membrane such that the advancing fluid sample does not cause movement of the non-diffusively bound reagent or non-diffusively bound control reagent from the place it is applied on these membranes. Conversely, by the term "diffusively bound" is meant placement on the absorbent membrane or reaction membrane such that the advancing fluid sample does cause movement of the diffusively bound labeled reagent from the place it is applied on these membranes.

As used herein, the term "fluid sample" refers to a material suspected of containing an analyte. The fluid sample can be used directly as obtained, for example, from any biological source. The fluid sample can also be obtained from an organism and the relevant portion extracted or dissolved into a solution. For example, the fluid sample can be a physiological fluid, such as, for example, saliva, ocular lens fluid, cerebral spinal fluid, sweat, blood, pus, mucus, serum, urine, milk, ascites fluid, synovial fluid, peritoneal fluid, amniotic fluid, and the like. In addition, the fluid sample fluid can be extracted from throat swabs, feces, or from other biological samples.

As used herein, the term "label" refers to a molecule that directly or indirectly mediates the production of a signal (such as a color change) which is used in assay procedures to indicate the presence or absence of analyte in a fluid sample. Labels may include enzymes, fluorescent molecules and will preferably include metal sols. Labels include colored latex spheres and colloidal metals. Labels include those disclosed by D. Yost et al., U.S. Pat. No. 4,954,452, issued Sep. 4, 1990; J. Leuvering, U.S. Pat. No. 4,313,734, issued Feb. 2, 1982; P. Tarcha et al., U.S. Pat. No. 5,252,459, issued Oct. 12, 1993; T. Gribnau et al., U.S. Pat. No. 4,373,932, issued Feb. 15, 1983; and R. Campbell, U.S. Pat. No. 4,703,013, issued Oct. 27, 1987 (each of which is incorporated by reference herein).

Alternatively, the label can be colored latex particles (see Campbell, U.S. Pat. No. 4,703,017, issued Oct. 27, 1987, which is incorporated by reference herein) or can be an enzyme that has reacted with a colorless substrate to give a colored product and is encapsulated, for example, in a liposome (see E. Soini, U.S. Pat. No. 5,518,883, issued May 21, 1996, which is incorporated herein by reference). The label may also be an inducible property of the particles, such as colorable latex particles (see Gribnau et al., U.S. Pat. No. 4,373,932, issued Feb. 15, 1983, and de Jaeger et al., U.S. Pat. No. 4,837,168, issued Jun. 6, 1989, both of which are incorporated by reference herein).

Alternatively, the label can be fluorescent molecules, such as the rhodamine, fluorescein, or umbelliferone series, employed by themselves or with a quencher molecule (see, for example, Ullman et al., U.S. Pat. No. 3,996,345, issued Dec. 7, 1976 and Tom et al., U.S. Pat. No. 4,366,241, issued Dec. 28, 1982, both of which are incorporated herein by reference). Chemiluminescent molecules, such as luminol, luciferin, lucigenin, or oxalyl chloride can be used as a signal means (see, for example, Maier, U.S. Pat. No. 4,104,029, issued Aug. 1, 1978, which is incorporated herein by reference). Finally, enzymatic systems that react with a colorless substrate to give a colored product, such as horseradish peroxidase, alkaline phosphatase, indoxyl phosphate and aminoethylcarbazole may be used as labels.

Diffusively bound complexed antibodies can be impregnated into the assay and within the absorbent membrane. The diffusively bound complexed antibodies are located upstream from a zone on the reaction membrane of the assay that contains immobilized antibodies. The diffusively bound label complexed antibodies bind to the analyte and are carried to the zone containing the immobilized antibodies where a sandwich antibody-hormone complex is formed and detected. However, if desired, both the diffusively bound and non-diffusively bound antibodies may be disposed on the same membrane.

In one embodiment, the diffusively bound labeled reagent will be labeled according to means known in the art. For purposes of producing a clearly visible reaction, labels of metal sols are preferred, with labels of colloidal gold or selenium being most preferred. An example of a suitable product is colloidal gold. These colloidal metals will produce colored reactions without addition of further reagents. However, fluorescent compounds (such as fluorescein and phycobiliprotein) and enzymes (such as those identified in U.S. Pat. No. 4,275,149, which is incorporated by reference herein), may also be used. To maximize contact of analyte with labeled reagent, the latter should be bound to the membrane across its face; i.e., from one side to the other. In addition, the labeled reagent should be bound to the membrane so that it is spatially separated from the absorbent sample pad when the absorbent sample pad is contacted with the absorbent membrane (see bar 125 shown in phantom on FIGS. 9, 10, 11, 12 and 13).

As used herein, the term "metal label" includes labels of metal sols; i.e., metal or metal compounds such as metal oxides, metal hydroxides, metal salts or polymer nuclei coated with a metal or metal compound. These metal labels may include dry forms of any of the above-named metals or metal compounds, and will preferably include colloidal gold in dry form. For example, the metal label can be composed of a metal sol, a selenium sol or a carbon sol (see, for example, Leuvering et al., U.S. Pat. No. 4,313,734, issued Feb. 2, 1982; Moremans et al., U.S. Pat. No. 4,775,636, issued Oct. 4, 1988; Yost et al., U.S. Pat. No. 4,954,452, issued Sep. 4, 1990; and Kang et al., U.S. Pat. No. 5,559,041, issued Sep. 24, 1996, each of which is incorporated by reference herein).

Depending on the context in which it is used, "reaction complex" or "complex" shall mean an a complex of analyte and diffusively bound labeled reagent complex first produced in the assay ("first complex"), a complex of the first complex and the non-diffusively bound reagent produced second in the assay ("second complex"), or the second complex and the non-diffusively bound control reagent produced third in the assay ("third complex"). In another embodiment of the analytical test device, "complex" shall mean a complex of analyte and non-diffusively bound reagent or a complex of the diffusively bound labeled reagent and non-diffusively bound reagent. The complex can be made up of a ligand-reagent pair that has spatial and/or polar features which permit it to bind specifically to each other. By "first member" of the complex is meant the member bound, covalently or non-covalently, at least to a sub-population of the particles. The "second member" of a complex refers to the corresponding binding member of the pair non-diffusively bound in the control region.

The term "display port" refers to any means whereby visual access to the reaction membrane can be gained. In one embodiment, a display port will be an aperture on the top positioned over the reaction membrane. The term also encompasses all or any part of the top that is made of a clear or transparent material so that the results can be seen. Thus, if the entire top is made of clear or transparent material, then the entire top can be referred to as the display port. In addition, there may be a clear or transparent membrane placed between the reaction membrane and the aperture of the display port so as to prevent evaporation of fluid sample, to prevent fluid sample or other fluid from entering the display port, or to prevent disruption of the membranes by touching, all of which can affect the performance of the assay.

The term "absorbent sample pad" refers to any material capable of containing the fluid sample and when contacted with the absorbent membrane produces an even fluid front along the absorbent membrane. For example, the edge of the absorbent sample pad that comes into contact with the absorbent membrane should be orthogonal to the absorbent membrane, ensuring that fluid sample will be applied evenly and at the same height across the membrane, thereby producing an even fluid front. The absorbent sample pad can be made from any bibulous, porous or fibrous material capable of absorbing fluid rapidly. The porosity of the material can be unidirectional or multidirectional. Porous plastic materials, such a polypropylene, polyethylene (preferably of high molecular weight), polyvinylidene fluoride, ethylene vinylacetate, acrylonitrile and polytetrafluoro-ethylene can be used. It can be advantageous to pre-treat the pad with a surface-active agent during manufacture to reduce any inherent hydrophobicity in the pad and, therefore, enhance its ability to take up and deliver a fluid sample rapidly and efficiently. The absorbent sample pad can also be made from paper or other cellulosic materials, such as nitro-cellulose. Preferably the material comprising the absorbent sample pad should be chosen such that the pad can be saturated with fluid sample within a matter of seconds. Also preferably, the material remains robust when moist, and for this reason, paper and similar materials are less preferred. In addition, by preferably providing a tight fit between the absorbent sample pad and the assembled top and bottom, the application of fluid sample to the absorbent sample pad will not result in fluid sample entering the device directly and by-passing the absorbent sample pad.

Also, the absorbent sample pad of the present invention is movable or "slidably insertable." As used herein, the term "slidably insertable" refers to the ability of the absorbent sample pad to be moved inside the device. In one embodiment of the device, the absorbent sample pad is disposed between the top and the bottom and can be slid inside the assembled top and bottom by the user (see FIG. 1). The absorbent sample pad will be in an container disposed between the top and bottom in the assembled device. The container is preferably made out of the same non-porous material as the top and bottom. In another embodiment of the device, the absorbent sample pad will be initially separate from the assembled top and bottom but insertable into the receiving port. The absorbent sample pad will preferably be complementary in shape for the receiving port such that when the absorbent sample pad is inserted into the receiving port and contacts the absorbent membrane, the analytical test device becomes substantially fluid-tight.

As used herein, the term "receiving port" refers to an aperture in the top, or the bottom or optionally an aperture in the top and the bottom together that allows the absorbent sample pad to enter the assembled top and bottom and contact the absorbent membrane. Preferably, the receiving port will be complementary in size to the absorbent sample pad to ensure a tight fit.

As used herein the term "container" refers to a material capable of supporting the absorbent sample pad. The container is preferably made of any suitable material that prevents the user from coming into direct contact with the fluid sample, which would otherwise contaminate the assay and make its use unpleasant. Specifically, the container in one embodiment of the invention is made of a non-porous material such as the commercially available "ABS" plastic (Monsanto Co., St. Louis, Mo.) comprising a top and a bottom (see FIGS. 1, 2, 3 and 4). It is also understood that the container could be in the shape of a stick, rod or tongue depressor.

Also, as used herein the term "stopping means" refers to a structure capable of stopping the movement of the container so that the absorbent sample pad is in direct fluid flow contact with the absorbent membrane but does not allow the absorbent sample pad to come into direct fluid flow contact with the reaction membrane. In one embodiment, the assembled top and bottom are the stopping means for the container. In another embodiment a horizontal bar on the bottom is the stopping means for the container.

The terms "absorbent membrane" and "reaction membrane" refer to any bibulous, porous or fibrous material capable of rapidly absorbing an aqueous fluid and conducting the fluid via capillary attraction. Suitable materials are described, for example, in H. J. Friesen, U.S. Pat. No. 4,861,711, issued Aug. 29, 1989; J. Bunting, U.S. Pat. No. 4,271,140, issued Jun. 2, 1981; May et al., U.S. Pat. No. 5,622,871, issued Apr. 22, 1997; May et al., U.S. Pat. No. 5,656,503, issued Aug. 12, 1997; May et al., U.S. Pat. No. 5,602,040, issued Feb. 11, 1997; and R. Rosenstein, U.S. Pat. No. 5,591,645, issued Jan. 7, 1997 (each of which is incorporated by reference herein). The preferred material for the absorbent membrane is a fiberglass product such as that marketed as "MANNIWEB" or "MANNIGLAS" by Lydall, Inc., Manchester, Conn. Other suitable materials include polyethylene or nitrocellulose pads and strips. The means for binding reagents to these materials are well-known in the art. Preferred porous materials include nitrocellulose, nylon, paper and silica gel. An advantage of a nitrocellulose membrane is that an immobilized antibody described above can be attached without prior chemical treatment. However, antibodies can be immobilized on other materials such as filter paper using well known chemical coupling methods such as, for example, CNBr, carbonyldimidazole or tresyl chloride. The reaction membrane will preferably be a chromatographic strip coated with gelatin to enhance the life of the strip and clarity of any visible reactions produced in the test.

The present invention also provides methods of using the analytical test device for detecting an analyte in a fluid sample, comprising adding fluid sample to the absorbent sample pad of the analytical test device, contacting the absorbent sample pad with the absorbent membrane and observing the reaction complex through the display port. Preferably, the reaction complex will be visible. Also preferably, there will be a first display port and a second display port.

DETAILED DESCRIPTION OF THE INVENTION

Figure 1:
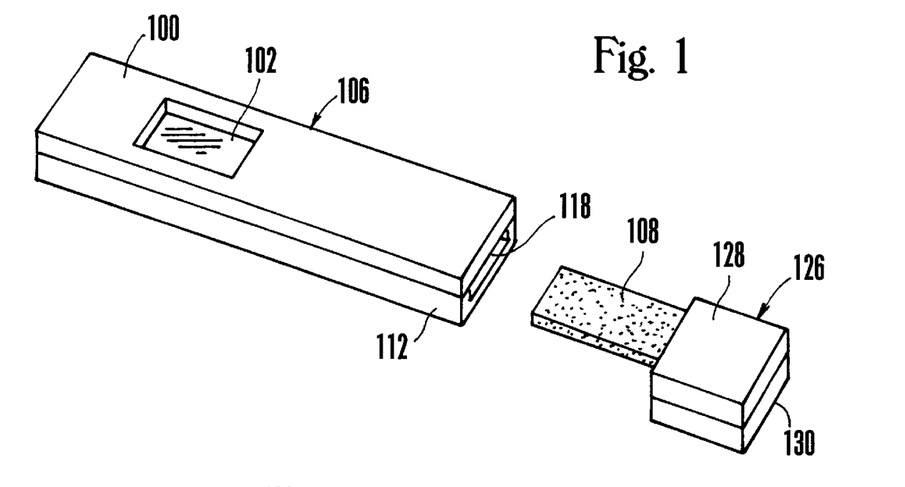
FIG. 1 is a perspective view of the analytical test device containing an absorbent sample pad in a container.

FIG. 1 shows a perspective view of one embodiment of an analytical test device for performing assays in accord with the invention. FIG. 1, therefore, depicts a housing 106 of rectangular shape, although any appropriate shape may be employed. Housing 106 is composed of two parts. The first is top 100, in which one opening appears, and the second is bottom 112. The opening through housing top 100 is display port 102 through which the test result can be viewed and compared. An opening through bottom 112 is receiving port 118. Absorbent sample pad 108 is in container 126. Container 126 is preferably composed of two parts, top 128 and bottom 130.

Figure 2:
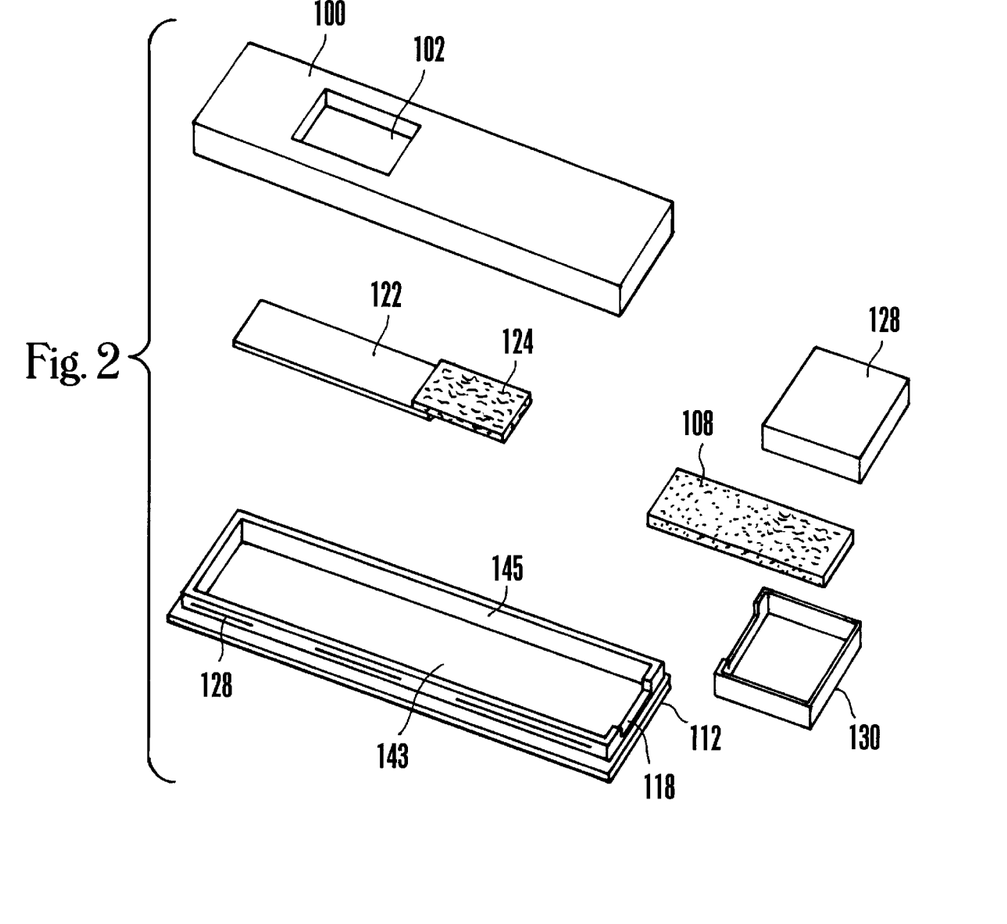
FIG. 2 is an exploded view showing the components of the analytical test device of FIG. 1.

FIG. 2 is an exploded view of the analytical test device of FIG. 1. In this view, it can be seen that bottom 112 contains floor 143, sidewalls 145, snaps 128 and receiving port 118. Contained within housing 106 will be membranes containing the reagents for carrying out the assay. In one embodiment there will be absorbent membrane 124 and reaction membrane 122. Absorbent membrane 124 and reaction membrane 122 will be in contact with, but need not be affixed, to each other. In addition, they will be disposed along floor 143 in the assembled device with absorbent membrane 124 toward receiving port 118 and reaction membrane 122 beneath display port 102. Absorbent sample pad 108 forms a separate part of the device which can be contacted with fluid sample, and then inserted through receiving port 118 to be in fluid flow contact with absorbent membrane 124.

Figure 3:
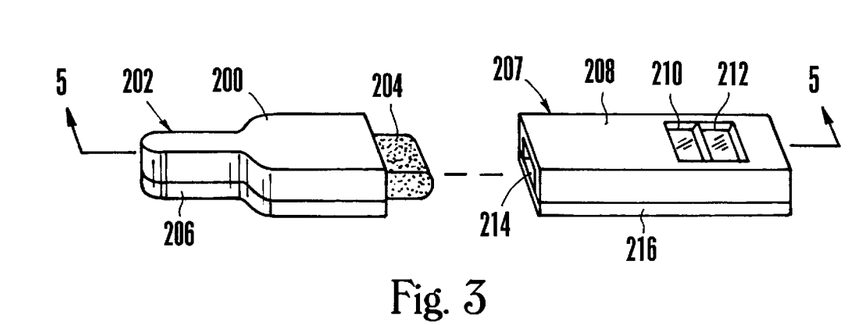
FIG. 3 is a perspective view of an embodiment of an analytical test device with an absorbent sample pad inside a container.

FIG. 3 shows a perspective view of another embodiment of the analytical test device for performing assays in accord with the invention. To that end housing 207 is composed of top 208, bottom 216, and has a first display port 210 and second display port 212 positioned on top 208, preferably in close proximity for ease of comparison of results. In addition, housing 208 has receiving port 214. Inside container 202, will be absorbent sample pad 204. Container 202 is preferably composed of top 200 and bottom 206.

Figure 4:
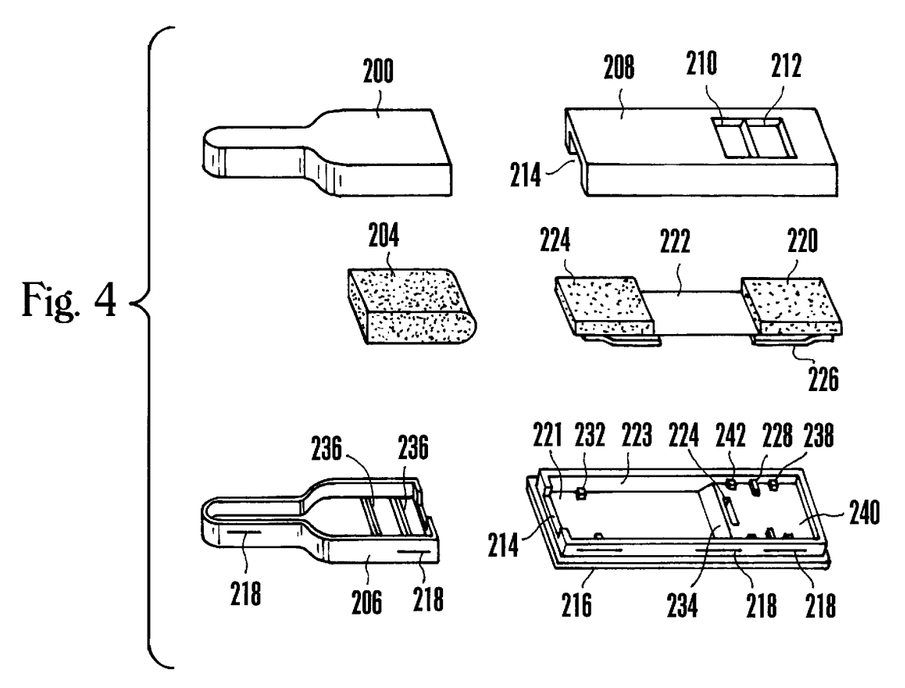
FIG. 4 is an exploded view showing the components of the analytical test device of FIG. 3.

FIG. 4 is an exploded view of the analytical test device shown in FIG. 3, and shows the components, top 208, bottom 216, lower plane 221, upper plane 240, slope 234, sidewalls 223, snaps 218, locating points 232, 242, 228 and 238, fluid gully 224, receiving port 214, and membranes containing the reagents for carrying out the assay, as described below. To that end, it can be seen that contained within housing 207 is absorbent membrane 224, reaction membrane 222 and collecting pad 220. Absorbent membrane 224 will be placed along lower plane 221 and along slope 234. Preferably, absorbent membrane 224 will be affixed to a nonporous substrate 226 such as vinyl coated paper or plastic coated paper by an adhesive or other suitable means. Substrate 226 will extend along upper plane 240 to form a surface to which reaction membrane 222 will be affixed. Absorbent membrane 224 and reaction membrane 222 will be in contact with, but need not be affixed, to each other. In another embodiment, absorbent membrane 224 will be split at its point of attachment to substrate 226 to extend above and below the substrate. This configuration serves to regulate the flow of fluid sample from absorbent membrane 224 to reaction membrane 222. Flow control can also be enhanced by placement of a well or fluid gully 224 below the junction between membranes 224 and 222. FIG. 4 also shows the placement of absorbent sample pad 204 in container 202 between top 200 and bottom 206, which are preferably held together by snaps 218. In addition, ridges 236 hold absorbent sample pad 204 in place.

Figure 5:
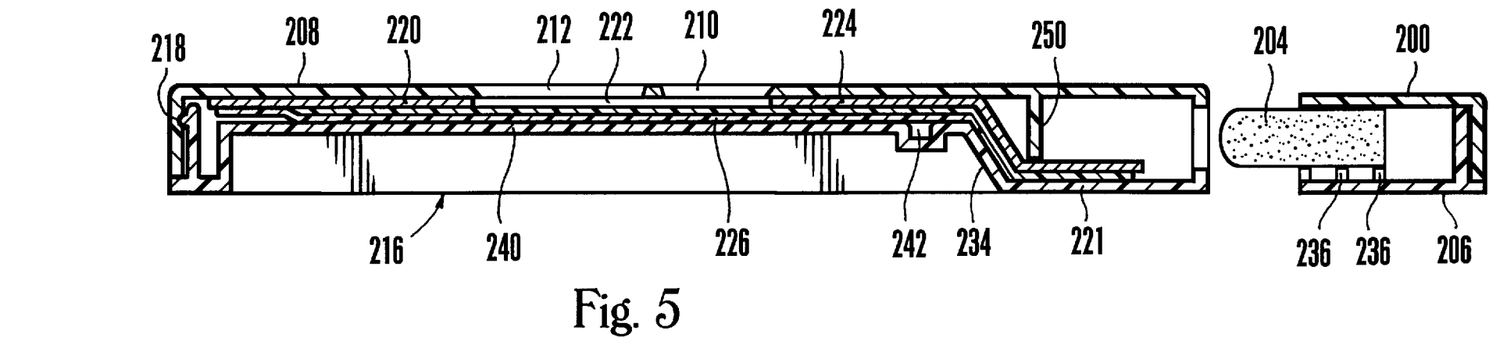
FIG. 5 is an enlarged sectional view along line 3—3 of the analytical test device of FIG. 3 showing that the absorbent sample pad is not in fluid flow contact with the absorbent membrane.

FIG. 5 is an enlarged sectional view along line 3—3 of the analytical test device shown in FIG. 3. In this view the orientation of absorbent sample pad 204 can be seen. Vertical bar 250 can be seen holding absorbent membrane 224 down to follow the contour of slope 234. Absorbent sample pad 204 is not in fluid flow contact with absorbent membrane 224 at this point. Thus, the user has the opportunity to add additional samples or reagents if desired.

Figure 6:
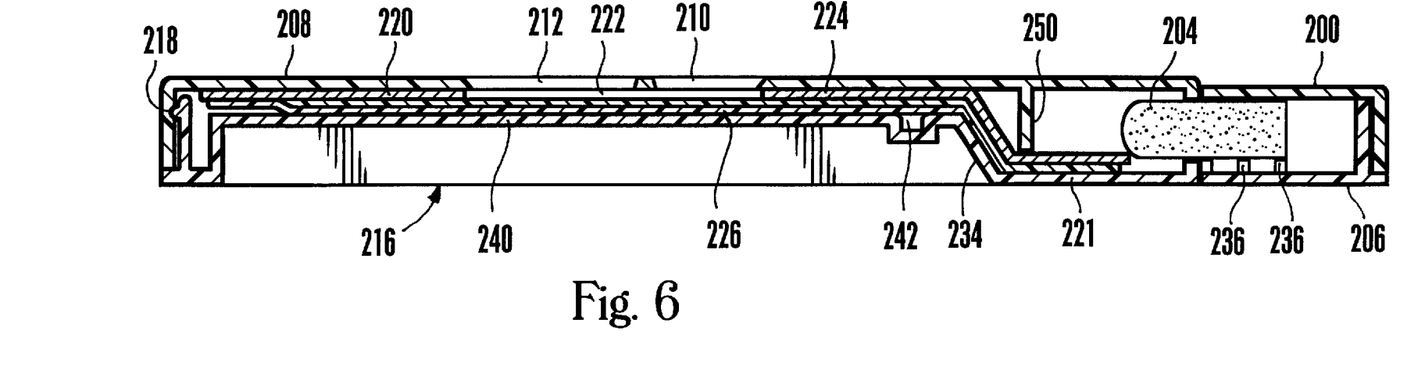
FIG. 6 is an enlarged sectional view along 3—3 of the analytical test device of FIG. 3 showing that the absorbent sample pad is in fluid flow contact with the absorbent membrane.

FIG. 6 is another enlarged sectional view along line 3—3 of the analytical test device shown in FIG. 3. In this view absorbent sample pad 204 is in fluid flow contact with absorbent membrane 224 after having been contacted with fluid sample, and then inserted into receiving port 214. Contact with absorbent membrane 324 will be indicated by a resistance. In this embodiment of the analytical test device, assembled top 208 and bottom 216 serve as stopping means for absorbent sample pad 204. Vertical bar 250 assures that absorbent membrane 224 is held down so that it can contact absorbent sample pad 204.

Figure 7:
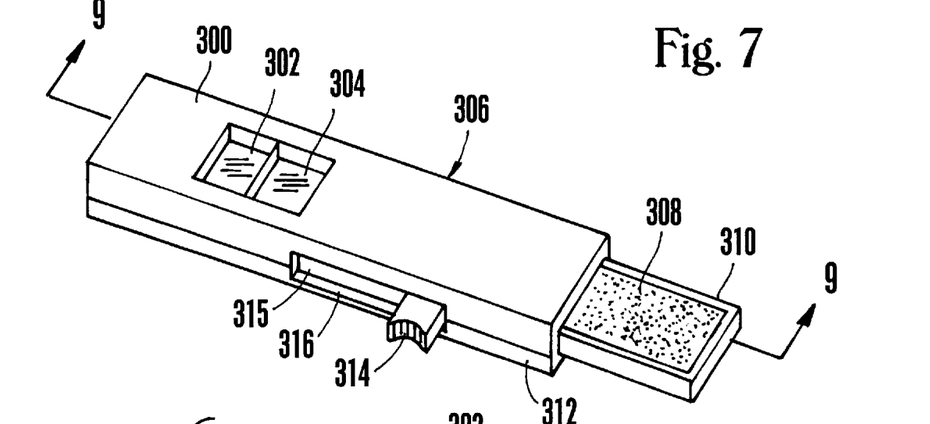
FIG. 7 is a perspective view of an embodiment of an analytical test device containing a slidably insertable absorbent sample pad in a container.

FIG. 7 shows a perspective view of another embodiment of the analytical test device. To that end, housing 306 is composed of top 300, bottom 312 and has first display port 304 and second display port 302 positioned on top 300, preferably in close proximity for ease of comparison of results. Housing 306 also has knob 314 that can be slid along groove 316 to stop point 315. Knob 314 is connected to and controls the movement of container 310 containing absorbent sample pad 308.

Figure 8:
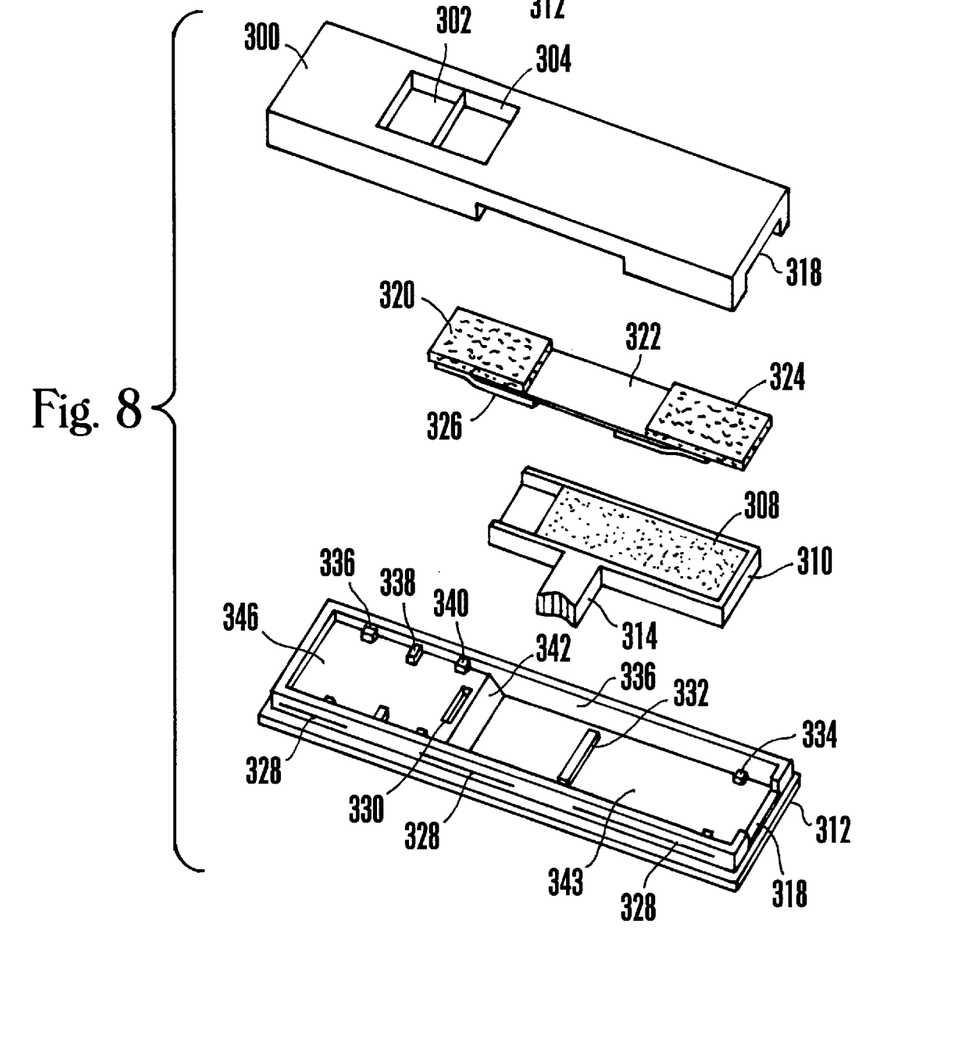
FIG. 8 is an exploded view showing the components of the analytical test device of FIG. 7.

FIG. 8 is an exploded view of the analytical test device shown in FIG. 7 and shows the components, bottom 312, sidewalls 336, snaps 328, slope 342, upper plane 346, lower plane 343, receiving port 318, stopping means 332, locating points 334, 336, 338 and 340, fluid gully 330 and membranes containing the reagents for carrying out the assay, as described below. To that end it can be seen that contained within housing 306 is absorbent membrane 324, reaction membrane 322 and collecting pad 320. Absorbent membrane 324 will be placed along lower plane 343 and along slope 342. Preferably, absorbent membrane 324 will be affixed to a nonporous substrate 326 such as vinyl coated paper or plastic coated paper by an adhesive or other suitable means. Substrate 326 will extend along upper plane 346 to form a surface to which reaction membrane 322 will be affixed. Absorbent membrane 324 and reaction membrane 322 will be in contact with, but need not be affixed, to each other. In another embodiment, absorbent membrane 324 will be split at its point of attachment to substrate 326 to extend above and below the substrate. This configuration serves to regulate flow of fluid sample from absorbent membrane 324 to reaction membrane 322. Flow control can also be enhanced by placement of a well or fluid gully 330 below the junction between membranes 324 and 322.

Figure 9:
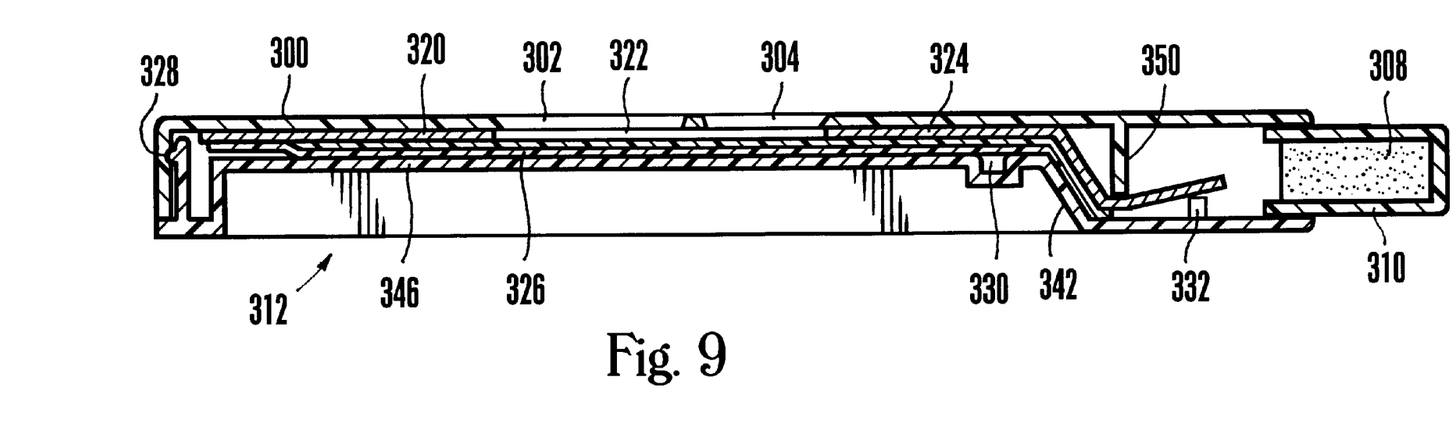
FIG. 9 is an enlarged sectional view along line 3—3 of the analytical test device of FIG. 7 showing initial placement of the absorbent sample pad not in fluid flow contact with the absorbent membrane.

FIG. 9 is an enlarged sectional view along line 3—3 of the analytical test device shown in FIG. 7. In this view the orientation of absorbent sample container 310, absorbent sample pad 308 and absorbent membrane 324 can be seen. Vertical bar 350 extends downward from the top and holds absorbent membrane 324 along slope 342. Stopping means 332 can also be seen. Fluid sample is added to absorbent sample pad 308. It can be seen that absorbent sample pad 308 is not in fluid flow contact with absorbent membrane 324 at this point. Thus, the user has the opportunity to add additional samples or reagents if desired.

Figure 10:
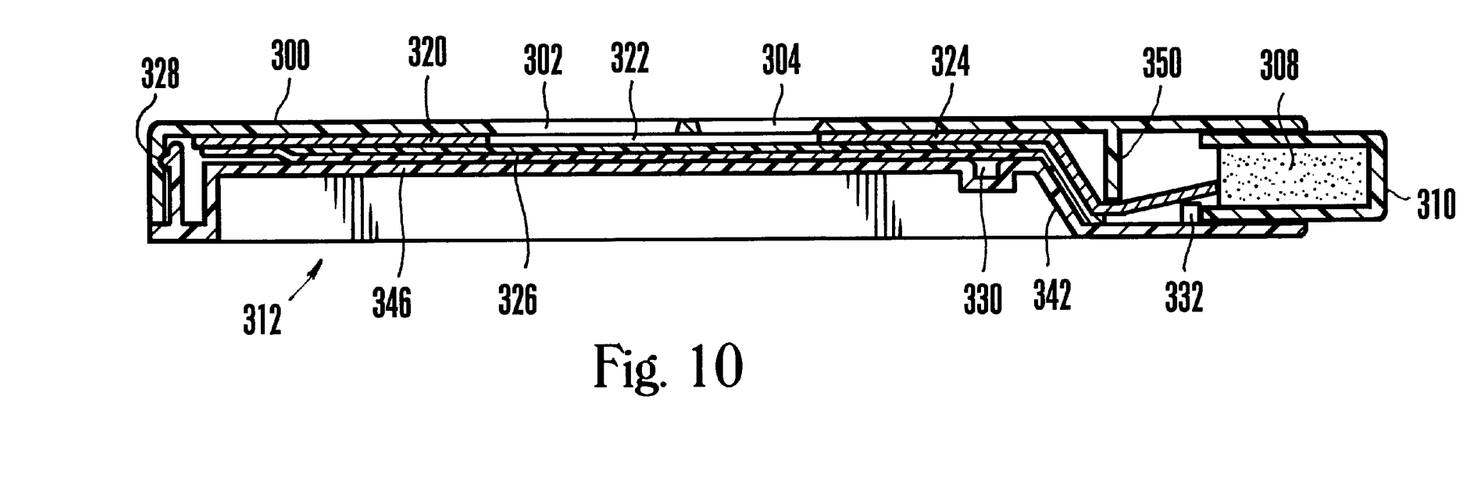
FIG. 10 is an enlarged sectional view along line 3—3 of the analytical test device of FIG. 7 showing placement of the absorbent sample pad in fluid flow contact with the absorbent membrane.

FIG. 10 is another enlarged sectional view along line 3—3 of the analytical test device shown in FIG. 7. It can be seen that absorbent sample pad 308 is in fluid flow contact with absorbent membrane 324 at this point, having been stopped by stopping means 332.

Figure 11:
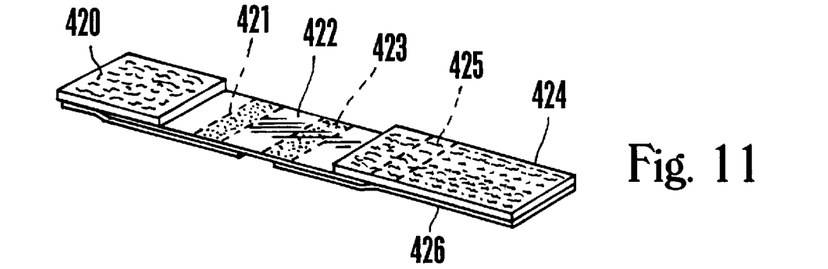
FIG. 11 is a perspective view of the absorbent and reaction membranes of the analytical test device employing a sandwich assay system showing a positive assay result.
Figure 12:
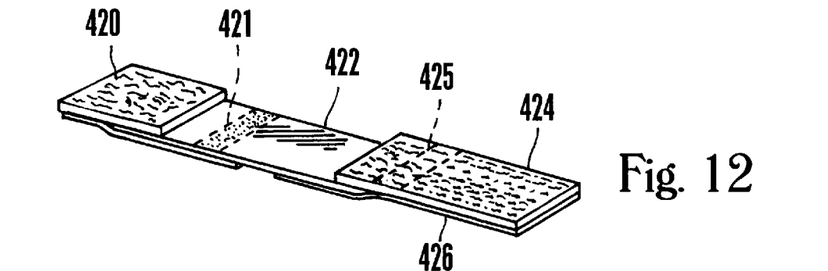
FIG. 12 is a perspective view of the absorbent and reaction membranes of the analytical test device employing a sandwich assay system showing a negative assay result.
Figure 13:
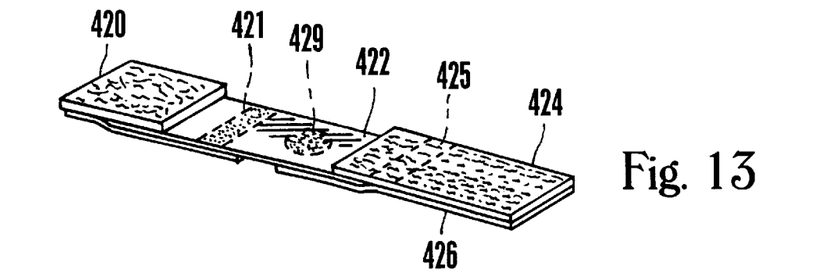
FIG. 13 is a perspective view of the absorbent and reaction membranes of the analytical test device employing a sandwich assay system showing an inconclusive assay result.

In FIGS. 11, 12 and 13, analyte in the fluid sample, if present, will bind to the diffusively bound labeled reagent at point 425 on absorbent membrane 424 to form a first complex. If desired, further fluid sample may be added up to the maximum binding capacity of unlabeled reagent and absorbency of the collecting pad material 420. The first complex and unbound first reagent, if any, will be carried along with the fluid sample by capillary action up to the reaction membrane 422. The position of the non-diffusively bound labeled reagent and first complex, if any, are indicated as 425 on FIGS. 11, 12 and 13.

All first complexes carried with the fluid sample will contact the reaction membrane 422. Fluid sample will pass through the reaction membrane 422, bringing the first complex, if any, into contact with the non-diffusively bound reagent to the reaction membrane 422 to bind therewith to form a second complex composed of first complex/non-diffusively bound reagent. If second complexes are formed, they will appear in the test region 427 (FIG. 12).

Fluid sample will continue its migration by wicking through reaction membrane 422 past the non-diffusively bound reagent to the non-diffusively bound control reagent. Diffusively bound labeled reagent not complexed to analyte will bind with the non-diffusively bound control reagent to form a third complex. The third complex will appear as display 421 in the control region (FIGS. 11, 12 and 13). Substrate 426 is also shown.

Formation of all complexes in the assay method described herein may be by sandwich or competitive immunoassay techniques well known to those skilled in the art. Within a predetermined time period, any second complex present and the third complex will produce a detectable signal mediated by the label. In one embodiment, the detectable signal will be a color change. This color change will signal either a positive (analyte present) or negative (analyte not present) reaction by providing two separate reactive regions within those portions of reaction membrane 422 visible to the user through the display ports.

Other control or comparative result signals may be provided, including signals that indicate whether an invalid result is obtained, by similar means known to those skilled in the art (see, for example, the signal system described in Brown et al., U.S. Pat. No. 5,160,701, issued Nov. 3, 1992, which is incorporated by reference herein).

As shown in FIG. 11, a positive result is indicated when color changes forming substantially similar shapes (in this instance, horizontal bars 421 and 423) appear. In contrast, as shown in FIG. 12, a negative result is indicated when a color change forming a distinguishable shape only appears, for example, as a horizontal bar 421. Finally, an inconclusive result is shown in FIG. 13, where color changes appear in both regions having substantially dissimilar shapes (i.e., horizontal bar 421 and smudge 429). In this latter instance, the user would be alerted that the test should be repeated. While due to the decreased impact of leading edge effects and similar phenomena in this assay it is not expected that inconclusive results will be frequent, the assay requires such a small application of fluid sample that repetition should not be problematic in most applications.

Figure 14:
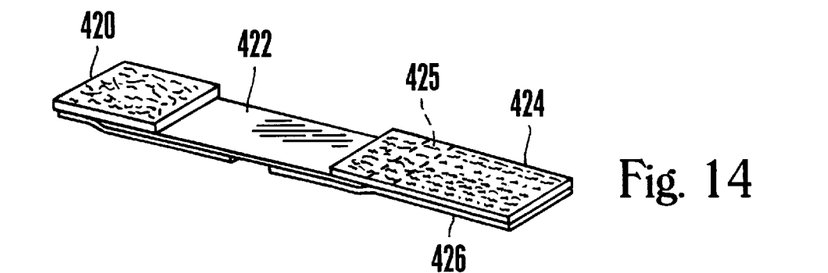
FIG. 14 is a perspective view of the absorbent and reaction membranes of an embodiment of the analytical test device employing a competitive assay system showing a positive assay result.
Figure 15:
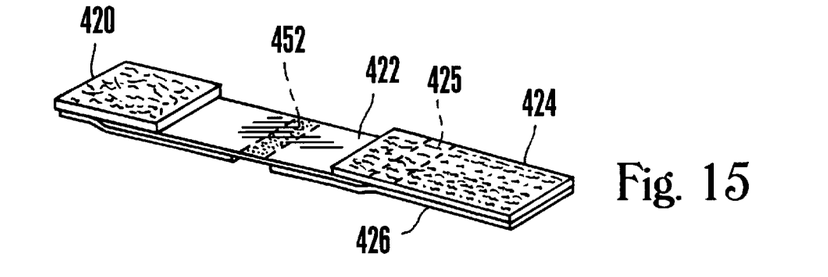
FIG. 15 is a perspective view of the absorbent and reaction membranes of an embodiment of the analytical test device employing a competitive assay system showing a negative assay result.

FIG. 14 and FIG. 15 show perspective views of the absorbent and reaction membranes wherein a competitive assay is employed. FIG. 14 shows a positive assay result, as indicated by no signal in the display port. FIG. 15 shows a negative assay result, as indicated by the presence of bar 452 in the display port.

EXAMPLE I

Analytical Test Device with Separate Absorbent Sample Pad

This example describes the method and analytical test device depicted in FIG. 3 containing a separate absorbent sample pad that is inserted into the receiving port.

This assay procedure is performed using anti-hCG antibody to form the second complex and an anti-hCG-colloidal gold compound to form the first complex. A fluid sample can be collected at any time of day, but for best results, it is best to test the first urine of the morning because it contains the highest concentration of hCG. The fluid sample is 1 cubic centimeter (hereinafter "cc") of urine suspected of containing hCG; the assay is performed at ambient temperatures not below 15° C. or exceeding 30° C. Absorbent sample pad 204 is placed into contact with a sample of urine, either by dipping it into a container containing at least 1 cc of urine, or by holding container 202 containing absorbent sample pad 204 into a stream of urine. Absorbent sample pad 204 is then inserted into receiving port 214 so that absorbent sample pad contacts absorbent membrane 224. Within 3 minutes visible color changes, (from pure white to pink) through substantially the center of display ports 210 and 212 on reaction membrane 222, are faintly visible. By the end of five minutes, a vividly pink bar symbol has appeared through substantially the center of each display port, indicating the presence of hCG in the fluid sample. All other visible areas of the reaction membrane visible through the second display port remain white, which is the normally visible color of the reaction membrane. This assay may be performed at any time after a suspected conception to determine the presence of hCG and, therefore, pregnancy.

EXAMPLE II

Analytical Test Device with Container Disposed Between Top and Bottom of Device

This example describes the method and analytical test device depicted in FIG. 7 containing a absorbent sample pad and container disposed between the top and bottom of the device.

The assay procedure is performed using anti-hCG antibody to form the second complex and an anti-hCG-colloidal gold compound to form the first complex. A fluid sample can be collected at any time of day, but for best results, it is best to test the first urine of the morning because it contains the highest concentration of hCG. The fluid sample is at least 1 cubic centimeter (hereinafter "cc") of urine suspected of containing hCG; the assay is performed at ambient temperatures not below 15° C. or exceeding 30° C. The 1 cc of urine is added to absorbent sample pad 308 by pipette. The container 310 is slid using knob 314 along groove 316 to its stop position 315. Within 3 minutes visible color changes, (from pure white to pink) through substantially the center of display ports 304 and 302 on reaction membrane 322, are faintly visible. By the end of five minutes, a vividly pink bar symbol has appeared through substantially the center of each display port, indicating the presence of hCG in the sample. All other visible areas of the reaction membrane visible through the second display port remain white, which is the normally visible color of the reaction membrane. This assay may be performed at any time after a suspected conception to determine the presence of hCG and, therefore, pregnancy.

Although the invention has been described with reference to the examples provided above, it should be understood that various modifications can be made without departing from the spirit of the invention. Accordingly, the invention is limited only by the claims.

What is claimed is:

1. An analytical test device, comprising a housing comprising:
    (a) a top having one or more display ports;
    (b) a bottom;
        I) the top or the bottom further having a receiving port or together the top and the bottom forming a receiving port for receiving a container comprising an absorbent sample receiving pad;
    (c) a test strip comprising an absorbent membrane, a reaction membrane having one or more reagents that form a reaction complex with an analyte in a fluid sample;
    (d) an absorbent sample receiving pad in a container; and
    (e) a stopping means,
    wherein the absorbent membrane and the reaction membrane are in fluid flow contact with one another; the strip is placed in the bottom such that the reaction membrane is visible through the one or more display ports and the absorbent membrane is towards the receiving port; and in the assembled top and bottom the absorbent sample receiving pad is slidably insertable through the receiving port until further insertion is stopped by the stopping means, which places the absorbent sample receiving pad in fluid flow contact with the absorbent membrane.

2. The analytical test device of claim 1, wherein the bottom further comprises a slope with an upper and lower end, and upper plan attached to the upper end of the slope, and a lower plane attached to the lower end of the slope.

3. The analytical test device of claim 2, wherein the top further comprises a vertical bar that deflects the absorbent membrane to follow the contour of the slope.

4. The analytical test device of claim 1, wherein the stopping means is the container contacting the outside of the assembled top and bottom at the receiving port.

5. The analytical test device of claim 1, wherein the bottom further comprises a horizontal bar inside the assembled top and bottom and is the stopping means.

6. The analytical test device of claim 5, wherein the stopping means is the horizontal bar contacting the container.

7. The analytical test device of claim 1, further containing one or more labeled reagents which migrates with the sample and are deposited on the absorbent membrane at a point spatially separated from the point at which the absorbent sample receiving pad first contacts the absorbent membrane.

8. The analytical test device of claim 7, wherein immobilized to the reaction membrane is:
    (a) an immobilized reagent complementary to an analyte in the fluid sample at a point beneath a first display port; and
    (b) an immobilized control reagent complementary to the labeled reagent at a point beneath a second display port.

9. The analytical test device of claim 7, wherein bound to the reaction membrane at a point beneath a first display port is an immobilized reagent, wherein the analyte and the labeled reagent compete for binding to the immobilized reagent, or wherein the immobilized reagent and the analyte compete for binding to the labeled reagent.

10. The analytical device of claim 1 further comprising a groove along one side of the housing and a knob connected to said container, wherein said knob slides along said groove to control movement of said container in said housing.

11. A method for detecting an analyte in a fluid sample, comprising the steps of:
    (a) adding the fluid sample to the absorbent sample receiving pad of the analytical test device claim 1;
    (b) inserting the absorbent sample receiving pad into the receiving port until the absorbent sample receiving pad is stopped by the stopping means;
    (c) detecting the analyte by observing a reaction complex through the one or more display ports.

12. The method according to claim 11, wherein the reaction complex is visible.

13. A method for detecting an analyte in a fluid sample using the device of claim 10, comprising the steps of:
 (a) sliding the container comprising the absorbent sample receiving pad into a position for receiving a sample;
 (b) adding fluid sample to the absorbent sample receiving pad;
 (c) sliding the container comprising the absorbent sample receiving pad into a position in fluid flow contact with the absorbent membrane;
 (d) detecting the analyte by observing a reaction complex through the one or more display ports.

* * * * *

UNITED STATES PATENT AND TRADEMARK OFFICE
CERTIFICATE OF CORRECTION

PATENT NO. : 6,140,136
DATED : October 31, 2000
INVENTOR(S) : Jin Po Lee

It is certified that error appears in the above-identified patent and that said Letters Patent is hereby corrected as shown below:

Column 2,
Line 43, please delete "3—3" and replace therefor with -- 5—5 --.
Line 47, please delete "3—3" and replace therefor with -- 5—5 --.
Line 56, please delete "3—3" and replace therefor with -- 9—9 --.
Line 60, please delete "3—3" and replace therefor with -- 9—9 --.

Column 12,
Line 57, please delete "3—3" and replace therefor with -- 5—5 --.
Line 65, please delete "3—3" and replace therefor with -- 5—5 --.

Column 13,
Line 43, please delete "3—3" and replace therefor with -- 9—9 --.
Line 54, please delete "3—3" and replace therefor with -- 9—9 --.

Signed and Sealed this

Fourteenth Day of January, 2003

JAMES E. ROGAN
*Director of the United States Patent and Trademark Office*

Adverse Decision in Interference

Patent No. 6,140,136, Jin Po Lee, ANALYTICAL TEST DEVICE AND METHOD OF USE, Interference No. 105,552, final judgment adverse to the patentee rendered September 7, 2007, as to claims 1-13.

*(Official Gazette July 29, 2008)*